United States Patent [19]

Campos et al.

[11] Patent Number: 5,496,405
[45] Date of Patent: Mar. 5, 1996

[54] PROCESS FOR THE PREPARATION OF ORGANIC PIGMENTS

[75] Inventors: Margot Campos, Charleston; Guenter Franke; Michael J. Greene, both of Mt. Pleasant, all of S.C.

[73] Assignee: Bayer Corporation, Pittsburgh, Pa.

[21] Appl. No.: 349,868

[22] Filed: Dec. 6, 1994

[51] Int. Cl.$^6$ .......................... C09B 48/00; C09B 67/52; C07D 471/02; C07D 221/18
[52] U.S. Cl. .......................... 106/495; 106/493; 106/494; 546/49; 546/56; 546/57; 546/58
[58] Field of Search ........................... 106/493, 495, 106/494; 546/49, 56, 57, 58

[56] References Cited

U.S. PATENT DOCUMENTS

| | | | |
|---|---|---|---|
| 3,157,659 | 11/1964 | Deuschel et al. | 546/56 |
| 3,256,285 | 6/1966 | Fuchs et al. | 546/28 |
| 3,257,405 | 6/1966 | Gerson et al. | 546/49 |
| 3,317,539 | 5/1967 | Jaffe | 546/57 |
| 4,758,665 | 7/1988 | Spietschka et al. | 106/504 |

FOREIGN PATENT DOCUMENTS 997476  7/1965  United Kingdom.

OTHER PUBLICATIONS

S. S. Labana and L. L. Labana, "Quinacridones", Chemical Reviews, vol. 67, pp. 1–18, Jan. 25, 1967.

*Primary Examiner*—Mark L. Bell
*Assistant Examiner*—Scott L. Hertzog
*Attorney, Agent, or Firm*—Joseph C. Gil; Richard E. L. Henderson

[57] ABSTRACT

This invention relates to a process for the preparation of quinacridone pigments comprising (a) heating, at a temperature of about 80° C. to about 145° C., a reaction mixture comprising
  (i) 2,5-dianilinoterephthalic acid or a 2,5-dianilinoterephthalic acid derivative having one or more substituents in at least one aniline ring,
  (ii) about 2 to about 10 parts by weight, relative to component (a)(i), of a dehydrating agent, and
  (iii) about 0.01 to about 10 percent by weight, relative to component (a)(i), of a salt other than an iron salt;
(b) drowning the reaction mixture from step (a) by adding said reaction mixture to about 3 to about 15 parts by weight, relative to component (a)(i), of a liquid in which the pigment is substantially insoluble;
(c) isolating the quinacridone pigment; and
(d) optionally, conditioning the quinacridone pigment.

12 Claims, No Drawings

PROCESS FOR THE PREPARATION OF ORGANIC PIGMENTS

BACKGROUND OF THE INVENTION

This invention relates to a process for the preparation of quinacridone pigments having reduced particle size and improved coloristic properties. In particular, the particle size of the typical unsubstituted quinacridone is reduced by about 30% by the addition of certain salts, preferably metal salts, to the ring closure melt during pigment synthesis and before the drowning process. The resultant quinacridones have characteristically deeper masstone, increased transparency, and generally bluer undertone (tint) hue.

Processes for the preparation of quinacridones are well known and documented. For example, S. S. Labana and L. L. Labana, "Quinacridones," *Chemical Reviews*, 67, 1–18 (1967), and U.S. Pat. Nos. 3,157,659, 3,256,285, and 3,317,539. The quinacridones thus obtained, known as crude quinacridones, are generally unsuitable for use as pigments and must undergo one or more additional finishing steps to modify the particle size, particle shape, or crystal structure to achieve pigmentary quality.

A preferred method for preparing quinacridones involves thermally inducing ring closure of 2,5-dianilinoterephthalic acid intermediates, as well as known aniline-substituted derivatives thereof, in the presence of polyphosphoric acid, such as described in U.S. Pat. No. 3,257,405. After ring closure is completed, the melt is drowned by pouring into a liquid in which the quinacridone is substantially insoluble, usually water or an alcohol. The resultant crystalline pigment that is then further conditioned by solvent treatment or milling in combination with solvent treatment.

Final particle size of quinacridone pigments is controlled by the methods used both in synthesis and in aftertreatment. Quinacridone pigments can be made more transparent by reducing the particle size or more opaque by increasing the particle size. Particle size is most often controlled during precipitation of the pigment by drowning or during subsequent milling of the crude pigment. Tinctorial strength and transparency of pigments can also be affected by solvent treatment.

Quinacridones and quinacridone solid solutions disclosed in the prior art are also sensitive to numerous other process variables, such as the type of drowning solvent, the temperature of the drowning solvent, the type of agitation used during the drowning process, the duration of the drowning process, and the post-drown processes. These variables are known to affect crystal phase, particle size and distribution, and surface characteristics, all of which ultimately affect the pigment color properties such as transparency, hue, tinctorial strength, dispersibility, dispersion stability, and rheology.

It is possible to obtain quinacridone pigments having smaller particle size by adding iron salts during the ring closure reaction beyond the amount of iron that is commonly introduced in small quantities during commercial preparation of the 2,5-dianilinoterephthalic acid precursor. E.g., copending application Ser. No. 08/239.180 (filed May 6, 1994). However, it has now been found that quinacridone pigments having smaller particle size can be obtained without the need for milling processes or the narrow, low-temperature ranges typically required in known processes by adding salts other than iron salts during the preparation of the pigments, particularly during the ring closure reaction. The process of the present invention is in principle applicable to all quinacridone pigment manufacturing processes that include an "acid pasting" step, but the greatest improvement in coloristic properties is observed with ring-closure processes, including processes used to prepare quinacridone solid solutions.

SUMMARY OF THE INVENTION

This invention relates to a process for the preparation of quinacridone pigments comprising (a) heating, at a temperature of about 80° C. to about 145° C. (preferably 100° C. to 130° C.) (preferably for about one to about 24 hours), a reaction mixture comprising
  (i) 2,5-dianilinoterephthalic acid or a 2,5-dianilinoterephthalic acid derivative having one or more substituents in at least one aniline ring,
  (ii) about 2 to about 10 parts by weight (preferably 3 to 8 parts by weight), relative to component (a)(i), of a dehydrating agent (preferably polyphosphoric acid), and
  (iii) about 0.01 to about 10 percent by weight (preferably 0.1 to 5 percent by weight, more preferably 0.25 to 3 percent by weight), relative to component (a)(i), of a salt other than an iron salt (preferably a metal salt);

(b) drowning the reaction mixture from step (a) by adding said reaction mixture to about 3 to about 15 parts by weight (preferably 5 to 10 parts by weight), relative to component (a)(i), of a liquid in which the pigment is substantially insoluble;

(c) isolating the quinacridone pigment; and (d) optionally, conditioning the quinacridone pigment.

DETAILED DESCRIPTION OF THE INVENTION

Quinacridone pigments are prepared according to the invention by first ring-closing 2,5-dianilinoterephthalic acid intermediates, including known aniline-substituted derivatives thereof, by heating such terephthalic acid intermediates in the presence of a dehydrating agent (preferably polyphosphoric acid) and a salt other than an iron salt. The quinacridone pigment is then drowned and isolated. The pigment is preferably also subjected to additional conditioning steps to improve pigmentary properties.

The process of the invention can be used to prepare unsubstituted quinacridone or ring-substituted quinacridone derivatives, depending on whether the ring closure is carried out using 2,5-dianilinoterephthalic acid or derivatives thereof having one or more substituents in at least one of the two aniline rings. Although essentially any 2,5-dianilinoterephthalic acid derivatives known in the art can be used, particularly preferred 2,5-dianilinoterephthalic acid derivatives are those in which both aniline moieties are substituted (typically with the same substituent) in the para position with groups such as halogen (especially chlorine), $C_1$–$C_6$ alkyl (especially methyl), and $C_1$–$C_6$ alkoxy (especially methoxy). It is also possible to use 2,5-dianilinoterephthalic acid derivatives in which both aniline moieties are substituted in the ortho or meta positions. Examples of suitable 2,5-dianilinoterephthalic acid derivatives include 2,5-di(4-chloroanilino)terephthalic acid, 2,5-di(4-methylanilino)terephthalic acid, and 2,5-di(4-methoxyanilino)terephthalic acid.

Ring closure step (a) is carried out in a dehydrating agent, particularly a strong acid such as polyphosphoric acid or acidic esters thereof (e.g., U.S. Pat. No. 4,758,665) or sulfuric acid. E.g., S.S. Labana and L.L. Labana, "Quinacridones," *Chemical Reviews*, 67, 1–18 (1967). Polyphosphoric acid having a phosphate content equivalent to about 110–120% $H_3PO_4$ is particularly preferred. When using polyphosphoric acid, the weight ratio of polyphosphoric acid to the terephthalic acid derivative is typically about 2:1 to about 10:1 (preferably 3:1 to 8:1). The lower ratios can give high viscosity reaction masses but are generally preferred because of cost considerations.

A critical feature of the present invention is the presence of a salt. (preferably a metal salt) other than an iron salt during the ring closure: reaction. Suitable salts should be at least partly soluble in the acidic reaction medium. Suitable metal salts include various salts of alkali metals (such as lithium, sodium, and potassium), alkaline earth metals (such as magnesium, calcium, and barium), aluminum, transition metals and heavy metals other than iron (such as nickel, cobalt, manganese, copper, and tin), including, for example, the halide (especially chloride), sulfate, nitrate, phosphate, polyphosphate, sulfonate (such as methane-sulfonate or p-toluenesulfonate, or even known quinacridone sulfonate derivatives), and carboxylate salts, as well as the oxides and hydroxides. Preferred metal salts contain an alkali or alkaline earth metal, more preferably an alkali metal. Hydrated salts can also be used.

Although generally less preferred, it is also possible to use essentially unreactive amine-based salts. Suitable amine-based salts include ammonium salts of the formula $R^aR^bR^cR^dN^+X^-$ in which $R^a$, $R^b$, $R^c$, and $R^d$ are independently hydrogen, $C_1$–$C_{20}$ alkyl, $C_7$–$C_{16}$ aralkyl, and other such hydrocarbon substituents, and X is a suitable anion, with the proviso that no more than one of the $R^a$, $R^b$, $R^c$, and $R^d$ groups can be hydrogen unless the remaining such groups are sufficiently sterically bulky to prevent significant reaction of the nitrogen (for example, with polyphosphoric acid to form a phosphoramide). Examples of such amine based salts include tetramethylammonium chloride or bromide, tetraethyl-ammonium chloride or bromide, tetrabutylammonium chloride or bromide, and methyltrioctylammonium chloride or bromide. Analogous tetralkyl-phosphonium salts can in principle also be used. Suitable amine-based salts also include unreactive monocyclic ammonium compounds containing one or more ring nitrogen atoms, preferably those having only tertiary or quaternary nitrogen atoms (such as protonated and/or alkylated salts of piperidine or piperazine), or unreactive bicyclic ammonium compounds containing one or more ring nitrogen atoms, preferably those having bridgehead nitrogen atoms (such as protonated and/or alkylated salts of quinuclidine).

It is also possible, although less preferred, to use metal complexes in which the metal, preferably a transition metal, is covalently bonded (that is, "complexed") to various ligands known in the art. When such complexes are used, it is generally preferred, although not essential, to use metal complexes that are stable under the acidic reaction conditions. When using a negatively charged ligand, the metal complex may even have an overall negative charge, such that a cationic rather than an anionic counterion must be present. Suitable metal complexes contain ligands such as water, halides (especially chloride), phosphates or polyphosphates, various polyhydroxyl compounds, β-diketones, and oxalate, and even ammonia, amines, or polyamines. In general, salts or hydrated salts instead of complexes are preferred.

Although much less preferred, it is also possible to include in the ring-closure reaction certain iron salts, preferably in quantities (based on the anhydrous iron salt) not exceeding 50% percent by weight relative to the non-ferrous salts used according to the invention. Suitable iron salts, if used at all, include various known iron(II) and iron(III) salts, including the sulfates, nitrates, phosphates, and halides (especially chloride), as well as oxides and hydroxides. It is also possible to use metal complexes containing iron(II) or iron(III). If iron salts are used at all, it is generally preferred to use salts or hydrated iron salts, especially hydrated iron(II) sulfates, rather than complexes. The commercial preparation of 2,5-di-anilinoterephthalic acid can itself introduce as much as 0. 1% by weight of iron, based on crude quinacridone pigment (although less than 0.06% by weight is more typical), which must be included in calculating the total amount of iron salt present in the process of the invention.

Although the commercial preparation of 2,5-dianilinoterephthalic acid can introduce small amounts of iron, a critical feature of the process of this invention is the addition of other salts to enhance the formation of quinacridone pigments having reduced particle size and improved coloristic properties. In particular, the process of the present invention requires a total salt content of about 0.01 to about 10 percent by weight relative to the 2,5-dianilinoterephthalic acid. Because high salt content is often detrimental to the quality of the finished good (for example, giving low color strength, poor dispersibility, and the like), large amounts of salts are generally to be avoided.

The reaction mixture is heated at a temperature of about 80° C. to about 145° C. (preferably 100° C. to 130° C.), preferably for about 1 to about 24 hours (more preferably for one to ten hours).

After ring closure step (a) is completed, the quinacridone pigment is precipitated (i.e., "drowned") in step (b) by adding the strongly acidic melt to a liquid in which the pigment is substantially insoluble, preferably water, a water-miscible solvent (such as methanol or other lower aliphatic alcohols), or mixtures thereof. Although it is possible to add the drowning liquid to the acidic melt (e.g., U.S. Pat. No. 3,265,699), the present invention is carried out only by adding the acidic melt to the solvent (compare U.S. Pat. No. 4,100,162).

Suitable drowning liquids include water and/or water-miscible organic liquids, including, for example, lower aliphatic alcohols, such as methanol; ketones and ketone alcohols, such as acetone, methyl ethyl ketone, and diacetone alcohol; amides, such as dimethylformamide and dimethylacetamide; ethers, such as tetrahydrofuran and dioxane; alkylene glycols and triols, such as ethylene glycol and glycerol; and other such organic liquids known in the art. Other organic liquids can be used but are generally less preferred.

Drowning some quinacridone pigments, particularly beta-phase unsubstituted quinacridone, with water alone or with alcohol mixtures containing more than about 50% by weight water can induce formation of undesirable amounts of the undesired alpha- and/or gamma-phase quinacridone pigments instead of beta-phase pigment or adversely affect particle size or shapes of the pigments. Therefore, for such pigments, drowning with $C_1$–$C_4$ aliphatic alcohols (preferably methanol) in admixture with up to about 50% by weight (preferably 10 to 25% by weight) of water is particularly preferred. In addition, solvents diluted with water in amounts approaching 50% by weight can provide economic advantages. Nevertheless, it is generally possible to drown quinacridone pigments with up to 100% by weight of water (optionally, of course, in admixture with a $C_1$–$C_4$ aliphatic alcohol) without such adverse effects. One skilled in the art could readily determine appropriate drowning conditions for a particular pigment.

The temperature of the drowning liquid is usually between about 5° C. and about 65° C., although temperature is less critical than in most known quinacridone processes. In general, lower drown temperatures give pigment having smaller particle size. However, because process cycle time is also very important (because of the manufacturing cost), a shorter drowning time is preferred and can be achieved without excessive particle size growth by allowing the solvent temperature to rise during the drowning process.

It is possible but less preferred to include a portion of the salt in the drown step.

The drowned pigment is then isolated in step (c) using methods known in the art, such as filtration, and then dried if desired. Other collection methods known in the art, such as centrifugation, are also suitable.

The crystalline pigment obtained in step (c) can be conditioned in optional step (d) using methods known in the art, such as solvent treatment or milling in combination with solvent treatment. Final particle size of the pigment can be controlled by varying the method of both synthesis and aftertreatment. For example, pigments can be made more transparent by reducing the particle size or more opaque by increasing the particle size. Particle size is most often controlled during precipitation of the pigment in the drowning liquid or during milling of the initially formed pigment.

Suitable milling methods include dry-milling methods such as sand-milling, ball-milling, and the like, with or without additives, or wet-milling methods such as salt-kneading, bead-milling, and the like in water or organic solvents, with or without additives.

Tinctorial strength and transparency of the pigment can also be affected by solvent treatment carried out by heating a dispersion of the pigment, often in the presence of additives, in a suitable solvent. Suitable solvents include organic solvents, such as alcohols, esters, ketones, and aliphatic and aromatic hydrocarbons and derivatives thereof, and inorganic solvents, such as water. Suitable additives include compositions that lessen or avoid flocculation, increase pigment dispersion stability, and reduce coating viscosity, such as polymeric dispersants (or surfactants) and various quinacridone derivatives. E.g., U.S. Pat. Nos. 4,455,173, 4,758,665, 4,844,742, 4,895,948, and 4,895,949.

Compared to previously known processes, pigments prepared according to the invention characteristically exhibit deeper or darker masstone, greater transparency, and distinctly lower undertone (i.e., bluer) hue, all of which are highly desirable characteristics of quinacridone pigments, especially when used for automobile colorant applications.

Because of their light stability and migration properties, the quinacridone pigments prepared according to the present invention are suitable for many different pigment applications. For example, pigments prepared according to the invention can be used as the colorant (or as one of two or more colorants) for very fast pigmented systems, such as mixtures with other materials, pigment formulations, paints, printing ink, colored paper, or colored macromolecular materials. The term "mixture with other materials" can be understood to include, for example, mixtures with inorganic white pigments, such as titanium dioxide (rutile) or cement, or other inorganic pigments. Examples of pigment formulations include flushed pastes with organic liquids or pastes and dispersions with water, dispersants, and, if appropriate, preservatives. Examples of paints in which pigments of this invention can be used include, for example, physically or oxidatively drying lacquers, stoving enamels, reactive paints, two-component paints, solvent- or water-based paints, emulsion paints for weatherproof coatings, and distempers. Printing inks include those known for use in paper, textile, and tinplate printing. Macromolecular substances include those of a natural origin, such as rubber; those obtained by chemical modification, such as acetyl cellulose, cellulose butyrate, or viscose; or those produced synthetically, such as polymers, polyaddition products, and polycondensates. Examples of synthetically produced macromolecular substances include plastic materials, such as polyvinyl chloride, polyvinyl acetate, and polyvinyl propionate; polyolefins, such as polyethylene and polypropylene; high molecular weight polyamides; polymers and copolymers of acrylates, methacrylates, acrylonitrile, acrylamide, butadiene, or styrene; polyurethanes; and polycarbonates. The materials pigmented with the quinacridone pigments of the present invention can have any desired shape or form.

Pigments prepared according to this invention are highly water-resistant, oil-resistant, acid-resistant, lime-resistant, alkali-resistant, solvent-resistant, fast to over-lacquering, fast to over-spraying, fast to sublimation, heat-resistant, and resistant to vulcanizing, yet give a very good tinctorial yield and are readily dispersible (for example, in plastic materials).

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

A rubout test was used for preliminary evaluation of color and appearance of the pigments. Dispersions were prepared on a Hoover Automatic Muller Model M4 (Hoover Color Corporation, Hiwassee, Va.) fitted with two glass plates and one 50-lb (ca. 22.5-kg) weight. For the masstone dispersion, 200 mg of dry pigment was added to 240 mg of raw linseed oil (distributed by United Specialties of America, Orlando, Fla.) and the mixture was placed on the bottom plate of the muller. After the upper plate was placed in contact with the lower plate, the bottom plate was allowed to turn for 50 revolutions. After the plates were separated, the paste on the upper plate was removed with a spatula and added to the bottom plate. This dispersion process was repeated three more times. The resultant paste was diluted with 480 mg of raw linseed oil and the muller dispersion process was repeated two times. A small amount of the resultant masstone dispersion was placed on a slide and evaluated in comparison with a comparison dispersion prepared by the same muller dispersion process.

The rubout test also included an undertone (tint) evaluation using 100 mg of the (final) masstone dispersion and 2.0 g of Zinc Oxide Bleach White W-3689 (Superior Printing Inks, New York, N.Y.). This mixing process was carried out using a spatula. The undertone was also compared to the comparison undertone dispersion.

Differences in hue and chroma of the masstone and undertone dispersions were measured using an Applied Color System Spectral Sensor (Hunt Associated Laboratories, Fairfax, Va.).

EXAMPLES 1–34

Preparative procedures

Examples 1–26 describe the preparation of unsubstituted quinacridone, Examples 27–31 describe the preparation of a dimethyl-substituted quinacridone, Example 32 describes the preparation of a solid solution of unsubstituted quinacridone and 2,9-dimethylquinacridone, and Examples 33–34 describe the preparation of a dichloro-substituted quinacridone. Examples 1 and 2 describe the general procedure for the preparation of unsubstituted quinacridone by ring closure of the unsubstituted 2,5-dianilinoterephthalic acid intermediate, Example 27 describes the general procedure for the preparation of 2,9-dimethylquinacridone by ring closure of the dimethyl-substituted 2,5-dianilinoterephthalic acid intermediate, Example 32 describes the preparation of a solid solution of unsubstituted quinacridone and 2,9-dimethylquinacridone by ring closure of a mixture of the unsubstituted and dimethyl-substituted 2,5-dianilinoterephthalic acid intermediates, and Example 33 describes the general procedure for the preparation of 2,9-dichloroquinacridone by ring closure of the dichloro-substituted 2,5-dianilinoterephthalic acid intermediate, with the ring closure step in each example being followed by aftertreatment of the crude pigment to form the respective pigmentary quinacridones. Quantities of the salts used in each Example according to the invention are given in each of Tables 1–5 as weight percents and mole percents relative to the dianilinoterephthalic acid intermediate.

EXAMPLES 1–26

Preparation of unsubstituted quinacridone

Examples 1–8 illustrate the preparation of pigmentary quinacridone according to the invention using sodium chloride (without and with water being added to the drowning liquid), and Examples 9–20 illustrate the preparation of pigmentan/quinacridone according to the invention using other salts or mixtures of salts (without and with water being added to the drowning liquid).

EXAMPLE 1

Pigmentary quinacridone was prepared according to the invention with sodium chloride being added to the reaction medium but without water being added to the drowning liquid.

To 270 g of polyphosphoric acid (117.4% phosphoric acid) heated at 80°–95° C. was added 0.25 g (4.3 mmole) of sodium chloride followed by 50 g (0.144 mole) of 2,5-dianilinoterephthalic acid having an iron content of less than 100 ppm. The mixture was heated at 120°–125° C. for four hours. After the viscous solution was cooled to 90°–95° C., the acid strength was adjusted to 107% by the dropwise addition of 75% phosphoric acid. The resultant melt was stirred for 20 minutes and then slowly poured into 400 g of methanol at 35° C. The temperature of the resultant slurry was allowed to rise during the addition to about 64° C., with the temperature being controlled during addition by external cooling and adjustment of melt addition rate. The slurry was heated at reflux (68°–72° C.) for one hour, diluted with 600 g of water, and stirred for 30 minutes. The solid component was collected by filtration and washed with water until acid-free. The resultant presscake was reslurried in 1000 g of aqueous sodium hydroxide and heated at about 85° C. The slurry was cooled, filtered, and washed with water until free of alkali, then reslurried in water and treated with aqueous sodium hydroxide containing naphthenic acid. The resultant slurry was heated at about 140°–145° C. in a closed system (e.g., a pressure reactor), cooled, acidified to pH 4.5–5.0 with phosphoric acid, and stirred. The solid component was collected by filtration and washed with water. The wet cake can be oven dried or used as is for specific applications. Here, the wet cake was dried in an oven at 60° C. to give about 40 g of quinacridone as a brilliant violet solid.

Based on a rub-out test in linseed oil (as described above), the pigment of Example 1 was bluer in undertone (tint) and significantly deeper in masstone than a comparison pigment prepared without the addition of a salt.

EXAMPLE 2

Pigmentary quinacridone was prepared according to the invention with sodium chloride being added to the reaction medium and water being added to the drowning liquid.

To 270 g of polyphosphoric acid (117.4% phosphoric acid) heated at 80°–95° C. was added 0.25 g (4.3 mmole) of sodium chloride followed by 50 g (0.144 mole) of 2,5-dianilinoterephthalic acid having an iron content of less than 100 ppm. The mixture was heated at 120°–125° C. for four hours. After the viscous solution was cooled to 90°–95° C., the acid strength was adjusted to 107% by the dropwise addition of 75% phosphoric acid. The resultant melt was stirred for 20 minutes and then slowly poured into a mixture of 360 g of methanol and 40 g of water (i.e., 90% aqueous methanol) at 35° C. The temperature of the resultant slurry was allowed to rise during the addition to about 64° C., with the temperature being controlled during addition by external cooling and adjustment of melt addition rate. The slurry was heated at reflux for one hour and diluted with 600 g of water. After the resultant slurry was stirred for 30 minutes, the solid component was collected by filtration and washed with water until acid-free. The resultant presscake was reslurried in 1000 g of aqueous sodium hydroxide, then heated at about 85° C. The slurry was cooled, filtered, and washed with water until free of alkali, then reslurried in water and treated with aqueous sodium hydroxide containing naphthenic acid. The resultant slurry was heated at about 140°–145° C. in a closed system (e.g., a pressure reactor), cooled, acidified to pH 4.5–5.0 with phosphoric acid, and stirred. The solid component was collected by filtration and washed with water. The wet cake can be oven dried or used as is for specific applications. Here, the wet cake was dried in an oven at 60° C. to give about 40 g of quinacridone as a brilliant violet solid.

Based on a rub-out test in linseed oil (as described above), the pigment of Example 2 was significantly bluer in undertone (tint) and deeper in masstone than a comparison pigment prepared without the addition of a salt.

EXAMPLES 3–8

Examples 3–8 were carried out according to the procedures of Example 1 (no water in the drowning liquid) and Example 2 (10% water in the drowning liquid) using the quantities of sodium chloride shown in Table 1. Based on a rub-out test in linseed oil (as described above), the pigments of Examples 3–8 were bluer in undertone (tint) and deeper in masstone than a comparison pigment prepared without the addition of a salt.

TABLE 1

Unsubstituted quinacridone according to Examples 1–8

| | Examples | | | | | | | |
|---|---|---|---|---|---|---|---|---|
| | 1 | 2 | 3 | 4 | 5 | 6 | 7 | 8 |
| Salt | NaCl | | NaCl | | NaCl | | NaCl | |
| Salt (weight %) | 0.5 | | 1.0 | | 1.5 | | 2.0 | |
| Salt (mole %) | 3.0 | | 6.0 | | 8.9 | | 11.9 | |
| Methanol (%) | 100 | 90 | 100 | 90 | 100 | 90 | 100 | 90 |

EXAMPLES 9–20

Examples 9–20 were carried out according to the procedures of Example 1 (when not using water in the drowning liquid) and Example 2 (when using 10% water in the drowning liquid) using salts other than sodium chloride in the quantities shown in Table 2. Based on a rub-out test in linseed oil (as described above), the pigments of Examples 9–20 were bluer in undertone (tint) and deeper in masstone than a comparison pigment prepared without the addition of a salt.

TABLE 2

Unsubstituted quinacridone according to Examples 9–20

| | Examples | | | | | | | | | | | |
|---|---|---|---|---|---|---|---|---|---|---|---|---|
| | 9 | 10 | 11 | 12 | 13 | 14 | 15 | 16 | 17 | 18 | 19 | 20 |
| Salt | $Na_2SO_4$ | | $K_2SO_4$ | | $CaSO_4$ | | $BaSO_4$ | | $CuSO_4.5 H_2O$ | | LiCl | |
| Salt (weight %) | 1.0 | | 1.0 | | 1.0 | | 2.0 | | 1.2 | | 1.0 | |
| Salt (mole %) | 2.4 | | 2.0 | | 2.6 | | 3.0 | | 1.7 | | 8.2 | |
| Methanol (%) | 100 | 90 | 100 | 90 | 100 | 90 | 100 | 90 | 100 | 90 | 100 | 90 |

EXAMPLES 21–26

Examples 21–26 were carried out according to the procedures of Example 1 (when not using water in the drowning liquid) and Example 2 (when using 10% water in the drowning liquid) using mixtures of various salts with ferrous sulfate heptahydrate in the quantities shown in Table 3. Based on a rub-out test in linseed oil (as described above), the pigments of Examples 21–26 were significantly deeper in masstone than a comparison pigment prepared without the addition of a salt.

TABLE 3

Unsubstituted quinacridone according to Examples 21–26

| | Examples | | | | | |
|---|---|---|---|---|---|---|
| | 21 | 22 | 23 | 24 | 25 | 26 |
| Salt A | NaCl | | NaCl | | $CaCl_2.H_2O$ | |
| Salt B | $FeSO_4.7 H_2O$ | | $FeSO_4.7 H_2O$ | | $FeSO_4.7 H_2O$ | |
| Salt A (wt. %) | 0.77 | | 1.7 | | 1.7 | |
| Salt A (mole %) | 4.6 | | 9.9 | | 3.9 | |
| Salt B (wt. %) | 1.1 | | 1.2 | | 0.5 | |
| Salt B (mole %) | 1.4 | | 1.6 | | 0.6 | |
| Methanol (%) | 100 | 90 | 100 | 90 | 100 | 90 |

EXAMPLES 27–31

Preparation of 2,9-dimethylquinacridone

Examples 27–31 illustrate the preparation of pigmentary 2,9-dimethylquinacridone according to the invention using various salts (without and with water being added to the drowning liquid).

EXAMPLES 27

Example 27 was carried out in a manner similar to Example 2 except for using a methyl-substituted dianilino-terephthalic acid in the presence of sodium sulfate.

To 320 g of polyphosphoric acid (111.8% phosphoric acid) heated at 80°–95° C. was added 0.72 g (5.1 mmole) of sodium sulfate followed by 72 g (0.1915 mole) of essentially salt-free 2,5-di(4-methylanilino)terephthalic acid. The mixture was heated at 120°–125° C. for two hours. The viscous solution was cooled to 90°–95° C. and then slowly poured into a mixture of 468 g of methanol and 52 g of water (i.e., 90% aqueous methanol) at 40° C. The temperature of the resultant slurry was allowed to rise during the addition to about 64° C., with the temperature being controlled during addition by external cooling and adjustment of melt addition rate. The slurry was heated at reflux for one hour, cooled to 60° C., and diluted with 600 g of water. After the slurry was stirred at 60° C. for 30 minutes, the solid component was collected by filtration and washed with water until acid-free.

The resultant presscake was reslurried in 800 g of aqueous sodium hydroxide, then heated at about 90°–95° C. The slurry was cooled, filtered, and washed with water until free of alkali, then reslurried in water. The resultant slurry was heated at 140°–145° C. in a closed system (e.g., a pressure reactor), cooled, acidified to pH 3.5 with phosphoric acid, treated with an aqueous emulsion of sodium dioctyl sulfosuccinate and VM&P Naphtha (available from Unocal Chemicals), and stirred. The solid component was collected by filtration and washed with water. The wet cake can be oven dried or used as is for specific applications. Here, the wet cake was dried in an oven at 60° C. to give about 60 g of 2,9-dimethylquinacridone as a brilliant magenta solid.

EXAMPLES 28–31

Examples 28–31 were carried out according to the procedure of Example 27 using potassium sulfate (without and with water being added to the drowning liquid) in the quantities shown in Table 4.

Based on a rub-out test in linseed oil (as described above), the pigments of Examples 27–31 were bluer in undertone (tint) and deeper in masstone than a comparison pigment prepared without the addition of a salt.

TABLE 4

2,9-Dimethylquinacridone according to Examples 27–31

|  | Examples | | | | |
| --- | --- | --- | --- | --- | --- |
|  | 27 | 28 | 29 | 30 | 31 |
| Salt | Na$_2$SO$_4$ | K$_2$SO$_4$ | | K$_2$SO$_4$ | |
| Salt (weight %) | 1.0 | 0.69 | | 1.4 | |
| Salt (mole %) | 2.7 | 1.5 | | 3.0 | |
| Methanol (%) | 90 | 100 | 90 | 100 | 90 |

EXAMPLE 32

Preparation of a solid solution of unsubstituted quinacridone and 2,9-dimethylquinacridone Example 32 describes the preparation of a solid solution of unsubstituted quinacridone and 2,9-dimethylquinacridone in which potassium sulfate was added to the reaction mixture and 100% water (i.e., with no methanol) was used as the drowning liquid.

To 300 g of polyphosphoric acid (117% phosphoric acid) heated at 80°–95° C. was added 0.6 g (3.4 mmole) of potassium sulfate followed by 15 g (0.043 mole) of 2,5-dianilinoterephthalic acid and 45 g (0.120 mole) of 2,5-di(4-methylanilino)terephthalic acid (i.e., 1.0 wt.% and 2.1 mol % of potassium surfate relative the total amount of the dianilinoterephthalic acid intermediates). The mixture was heated at 120°–125° C. for two hours. The viscous solution was cooled to 90°–95° C. and then slowly poured into 1200 g of water at 25° C. The temperature of the resultant slurry was allowed to rise during the addition to about 40° C., with the temperature being controlled during addition by external cooling and adjustment of melt addition rate. After the resultant slurry was stirred for one hour at ambient temperature, the solid component was collected by filtration and washed with water until acid-free. The presscake was reslurried in water, the pH was adjusted to 9.0 using aqueous sodium hydroxide, and methanol was added. The resultant slurry was heated at 115°–120° C. in a closed system (e.g., a pressure reactor). After the slurry was cooled to ambient temperature, the solid component was collected by filtration and washed with water. The wet cake can be oven dried or used as is for specific applications. Here, the wet cake was dried in an oven at 60° C. to give about 50 g of the solid solution as a brilliant magenta solid.

Based on a rub-out test in linseed oil (as described above), the pigment of Example 32 was bluer in undertone (tint) and significantly deeper in masstone than a comparison pigment prepared without the addition of a salt.

EXAMPLES 33–34

Preparation of 2,9-dichloroquinacridone

Examples 33 and 34 illustrate preparations of pigmentary 2,9-dichloroquinacridone according to the invention using sodium chloride (with and without water being added to the drowning liquid).

EXAMPLE 33

Example 33 was carried out with sodium chloride being added to the reaction medium and water being added to the drowning liquid.

To 300 g of polyphosphoric acid (116% phosphoric acid) heated at 80°–95° C. was added 1.0 g (17.1 mmole) of sodium chloride followed by 50 g (0.12 mole) of 2,5-di(4-chloroanilino)terephthalic acid. The mixture was heated at 110°–115° C. for five hours. After the viscous solution was cooled to 90°–95° C., the acid strength was adjusted to 110.5% by the dropwise addition of 75% phosphoric acid. The resultant melt was stirred for 20 minutes and then slowly poured into a mixture of 324 g of methanol and 36 g of water (i.e., 90% aqueous methanol) at 35° C. The temperature of the resultant slurry was allowed to rise during the addition to about 64° C., with the temperature being controlled during addition by external cooling and adjustment of melt addition rate. The slurry was heated at reflux for one hour and diluted with 280 g of water. After the resultant slurry was stirred for 30 minutes, the solid component was collected by filtration and washed with water until acid-free. The press-cake was reslurried in water, the pH was adjusted to 8.5 using aqueous sodium hydroxide, and methanol was added. The resultant slurry was heated at about 120° C. in a closed system (e.g., a pressure reactor). After the slurry was cooled to ambient temperature, the solid component was collected by filtration and washed with water until neutral. The wet cake can be oven dried or used as is for specific applications. Here, the wet cake was dried in an oven at 60° C. to give about 43 g of 2,9-dichloroquinacridone as a brilliant magenta solid.

Based on a rub-out test in linseed oil (as described above), the pigment of Example 33 was deeper in masstone than a comparison pigment prepared without the addition of a salt.

EXAMPLES 34

Example 34 was carried out according to the procedure of Example 33 except for omitting the water from the drowning liquid.

TABLE 5

2,9-Dichloroquinacridone according to Examples 33–34

|  | Examples | |
| --- | --- | --- |
|  | 33 | 34 |
| Salt | NaCl | |
| Salt (weight %) | 2.0 | |
| Salt (mole %) | 10.0 | |
| Methanol (%) | 90 | 100 |

EXAMPLES 35–37

Applications

Examples 35–37 describe the preparation of various pigmented materials containing pigments prepared according to the invention.

EXAMPLE 35

Preparation of an enamel paint

A finely divided 8 g sample of the pigment prepared according to Example 27 was dispersed in 92 g of a stoving enamel having the following composition:
33% alkyd resin (e.g., AROPLAZ® 1453-X-50 alkyd resin, Reichhold Chemicals, Inc., White Plains, N.Y.)
15% melamine resin (e.g., RESIMENE® BM-7507 melamine resin, Monsanto Company, St. Louis, Mo.)

5% glycol monomethyl ester
34% xylene
13% butanol

Upon completion of the dispersion the pigmented paint was applied to a metal foil and then baked at 130° C. for 30 minutes. A magenta coating was obtained.

Other suitable alkyd resins are products based on synthetic or vegetable fatty acids, such as coconut oil, castor oil, linseed oil or the like. Urea resins can be used instead of melamine resins.

EXAMPLE 36

Preparation of a thermoplastic molding

A 0.2 g samples of the pigment prepared according to Example 27 was dispersed in 65 g of stabilized polyvinyl chloride and 35 g of diisooctyl phthalate at 160° C. in a mixing mill. A magenta film was obtained.

Synthetic polyamides of caprolactam or of adipic acid and hexamethylenediamine or the polyester condensates of terephthalic acid and ethylene glycol can be colored in a similar manner at 280°–300° C. (in an atmosphere of nitrogen where necessary).

EXAMPLE 37

Preparation of metallic paints

A mixtures of 6 g of the pigment prepared according to Example 27 in 12 g of xylene, 4.1 g of butyl acetate, 0.7 g of butanol, and 22.5 g of a 20% solution of cellulose acetobutyrate in 2:1 butyl acetate/xylene was dispersed by agitating for 30 minutes in a shaker containing 2 to 3 mm diameter glass beads. To the dispersion was then added 10 g of a saturated polyester resin (available as DYNAPOL® H 700 from Hüls America), 7.3 g of melamine resin, 8.7 g of a 20% solution of cellulose acetobutyrate in 2:1 butyl acetate/xylene, 18 g of butyl acetate, 1.6 g of butanol, and 9.7 g of xylene and shaking was continued for another 5 minutes.

Metallic paints were then prepared by adding a dispersion of aluminum paste (60% solids; available as SPARKLE SILVER® AR from Silberline Manufacturing Co., Inc.) in xylene (about 1:2) in amounts such that the ratio of pigment to aluminum was between about 80:12 and 1:99.

These metallic paints were applied to panels and after drying were coated with a clearcoat based on an acrylate/melamine resin (which can contain additional additives, such as ultraviolet absorbers). Brilliant metallic magenta paints were obtained.

What is claimed is:

1. A process for the preparation of quinacridone pigments comprising
   (a) heating, at a temperature of about 80° C. to about 145° C., a reaction mixture comprising
      (i) 2,5-dianilinoterephthalic acid or a 2,5-dianilinoterephthalic acid derivative having one or more substituents in at least one aniline ring,
      (ii) 2 to 10 parts by weight per 1 part by weight of component (a)(i), of a dehydrating agent, and
      (iii) 0.01 to 10 percent by weight, relative to component (a)(i), of a salt other than an iron salt;
   (b) drowning the reaction mixture from step (a) by adding said reaction mixture to 3 to 15 parts by weight, relative to component (a)(i), of a liquid in which the pigment is substantially insoluble;
   (c) isolating the quinacridone pigment; and
   (d) optionally, conditioning the quinacridone pigment.

2. A process according to claim 1 wherein step (a) is carried out at a temperature of 100° C. to 130° C.

3. A process according to claim 1 wherein the dehydrating agent (a)(ii) is polyphosphoric acid.

4. A process according to claim 3 wherein 3 to 8 parts by weight, per 1 part by weight of component (a)(i), of polyphosphoric acid are used in step (a).

5. A process according to claim 1 wherein 0.1 to 5 percent by weight, relative to component (a)(i), of salt (a)(iii) is used.

6. A process according to claim 1, wherein salt (a)(iii) is a metal salt other than an iron salt, optionally in admixture with an iron salt.

7. A process according to claim 1 wherein salt (a)(iii) is a salt of an alkali metal or an alkaline earth metal.

8. A process according to claim 1 wherein salt (a)(iii) is a salt of lithium, sodium, potassium, magnesium, calcium, or barium or a hydrate thereof.

9. A process according to claim 1 wherein salt (a)(iii) is a halide or a sulfate salt of lithium, sodium, potassium, magnesium, calcium, or barium or a hydrate thereof.

10. A process according to claim 1 wherein drowning step (b) is carried out using a $C_1$–$C_4$ aliphatic alcohol in admixture with 0 to 50% by weight of water.

11. A process according to claim 10 wherein the $C_1$–$C_4$ aliphatic alcohol is methanol.

12. A process according to claim 1 for the preparation of a quinacridone pigment other than a beta-phase unsubstituted quinacridone pigment wherein drowning step (b) is carried out using 100% water or water in admixture with less than 50% by weight of a $C_1$–$C_4$ aliphatic alcohol.

* * * * *